United States Patent [19]

Gordon et al.

[11] Patent Number: 4,524,212

[45] Date of Patent: Jun. 18, 1985

[54] ACYLOXYKETONE SUBSTITUTED IMINO AND AMINO ACIDS

[75] Inventors: Eric M. Gordon, Pennington; Jollie D. Godfrey, Jr., Lawrenceville, both of N.J.

[73] Assignee: E. R. Squibb & Sons, Inc., Princeton, N.J.

[21] Appl. No.: 423,875

[22] Filed: Sep. 27, 1982

[51] Int. Cl.³ .................. C07D 207/20; C07D 207/09
[52] U.S. Cl. ..................... 548/533; 546/147; 546/275; 548/201; 548/409; 548/492; 548/517; 548/525; 548/527; 260/239 A; 560/39; 560/170; 562/444; 562/567; 514/422; 514/423; 514/365; 514/416; 514/307; 514/330; 514/210
[58] Field of Search ............... 548/533, 517, 527, 525; 546/275

[56] References Cited

U.S. PATENT DOCUMENTS

| | | | |
|---|---|---|---|
| 4,053,651 | 10/1977 | Ondetti et al. | 424/319 |
| 4,105,776 | 8/1978 | Ondetti et al. | 424/274 |
| 4,129,566 | 12/1978 | Ondetti et al. | 546/326 |
| 4,154,935 | 5/1979 | Ondetti et al. | 546/189 |
| 4,192,878 | 3/1980 | Ondetti | 424/270 |
| 4,217,359 | 8/1980 | Krapcho | 424/274 |
| 4,234,489 | 11/1980 | Ondetti et al. | 260/326.42 |
| 4,256,751 | 3/1981 | Hayashi et al. | 424/258 |
| 4,296,033 | 10/1981 | Petrillo et al. | 260/326.2 |
| 4,296,113 | 10/1981 | Ondetti | 424/246 |
| 4,310,461 | 1/1982 | Krapcho et al. | 260/326.2 |
| 4,311,697 | 1/1982 | Krapcho | 424/240 |
| 4,316,905 | 2/1982 | Krapcho | 424/274 |
| 4,316,906 | 2/1982 | Ondetti et al. | 424/274 |
| 4,329,473 | 5/1982 | Almquist et al. | 546/281 |
| 4,337,201 | 6/1982 | Petrillo | 548/413 |
| 4,444,765 | 4/1984 | Karanewsky et al. | 424/200 |
| 4,448,772 | 5/1984 | Karanewsky et al. | 424/200 |
| 4,452,791 | 6/1984 | Ryono et al. | 424/200 |

FOREIGN PATENT DOCUMENTS

| | | |
|---|---|---|
| 868532 | 6/1978 | Belgium . |
| 45161 | 2/1982 | European Pat. Off. . |
| 2027025 | 2/1980 | United Kingdom . |
| 2048863 | 12/1980 | United Kingdom . |

OTHER PUBLICATIONS

Almquist et al., "Synthesis and Biological . . . ", J. Med. Chem., 1980, vol. 23, pp. 1392–1398.

Meyer et al., "Novel Synthesis of . . . ", J. Med. Chem., 1981, vol. 24, pp. 964–969.

Primary Examiner—Joseph Paul Brust
Attorney, Agent, or Firm—Lawrence S. Levinson; Stephen B. Davis

[57] ABSTRACT

Acyloxyketone substituted imino and amino acids of the formula

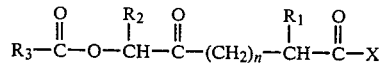

are disclosed. These compounds are useful hypotensive agents due to their angiotensin converting enzyme inhibition activity.

10 Claims, No Drawings

ACYLOXYKETONE SUBSTITUTED IMINO AND AMINO ACIDS

BACKGROUND OF THE INVENTION

Almquist et al., "Synthesis and Biological Activity of a Ketomethylene Analogue of a Tripeptide Inhibitor of Angiotensin Converting Enzyme", J. Med. Chem., 1980, 23, 1392–1398, disclose the ketomethylene compound of the formula

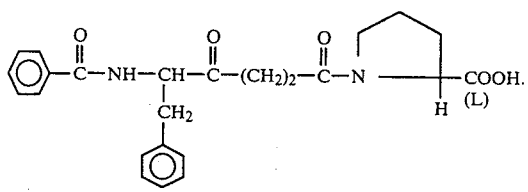

This and related compounds are also disclosed by Almquist et al. in U.S. Pat. No. 4,329,473.

Meyer et al., "Novel Synthesis of (S)-1-[5-(Benzoylamino)-1,4-dioxo-6-phenylhexyl]-L-proline and Analogues: Potent Angiotensin Converting Enzyme Inhibitors", J. Med. Chem., 1981, 24, 964–969, disclose the synthesis and activity of compounds of the formula

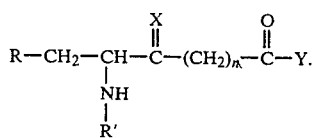

Gravestock et al. in European Patent Application No. 45161 disclose hypotensive compounds of the formula

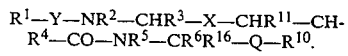

Mercaptoacyl derivatives of proline and substituted prolines are known to be useful hypotensive agents due to their angiotensin converting enzyme inhibition activity. Ondetti, et al. in U.S. Pat. No. 4,105,776 disclose such compounds wherein the proline ring is unsubstituted or substituted by an alkyl or hydroxy group. Ondetti, et al. in U.S. Pat. No. 4,154,935 disclose such compounds wherein the proline ring is substituted with one or more halogens. Ondetti, et al. in U.S. Pat. No. 4,316,906 disclose such compounds wherein the proline ring is substituted by various ethers and thioethers. Krapcho in U.S. Pat. No. 4,217,359 disclose such compounds wherein the proline ring has a carbamoyloxy substituent. Krapcho in U.S. Pat. No. 4,311,697 discloses compounds wherein the proline ring has a diether, dithioether, ketal or thioketal substituent in the 4-position. Krapcho in U.S. Pat. No. 4,316,905 discloses such compounds wherein the proline ring has a cycloalkyl, phenyl, or phenyl-lower alkylene substituent. Ondetti, et al. in U.S. Pat. No. 4,234,489 disclose such compounds wherein the proline has a keto substituent in the 5-position. Krapcho, et al. in U.S. Ser. No. 162,341 filed June 23, 1980, now U.S. Pat. No. 4,310,461, disclose such compounds wherein the proline has an imido, amido, or amino substituent in the 4-position. Iwao, et al. in U.K. Patent Application No. 2,027,025 disclose such compounds wherein the proline has an aromatic substituent in the 5-position.

Mercaptoacyl derivatives of 3,4-dehydroproline are disclosed as angiotensin converting enzyme inhibitors by Ondetti in U.S. Pat. No. 4,129,566. Mercaptoacyl derivatives of thiazolidinecarboxylic acid and substituted thiazolidinecarboxylic acid are disclosed as angiotensin converting enzyme inhibitors by Ondetti in U.S. Pat. No. 4,192,878 and by Yoshitomo Pharmaceutical Ind. in Belgium Pat. No. 868,532.

Mercaptoacyl derivatives of dihydroisoindole carboxylic acids and tetrahydroisoquinoline carboxylic acids are disclosed as being useful hypotensive agents by Ondetti, et al., in U.S. Ser. No. 69,031, filed Aug. 23, 1979. These mercaptoacyl tetrahydroisoquinoline compounds are also disclosed by Portlock in U.K. Application No. 2,048,863 and by Hayashi, et al. in U.S. Pat. No. 4,256,751.

Mercaptoacyl derivatives of various amino acids are disclosed by Ondetti, et al. as being useful hypotensive agents due to their angiotensin converting enzyme inhibition activity in U.S. Pat. No. 4,053,651.

SUMMARY OF THE INVENTION

The novel acyloxyketone substituted amino and imino acids, esters, and salts of this invention are of the formula

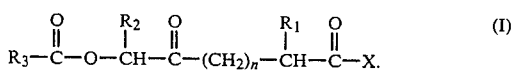

X is an amino or imino acid or ester of the formula

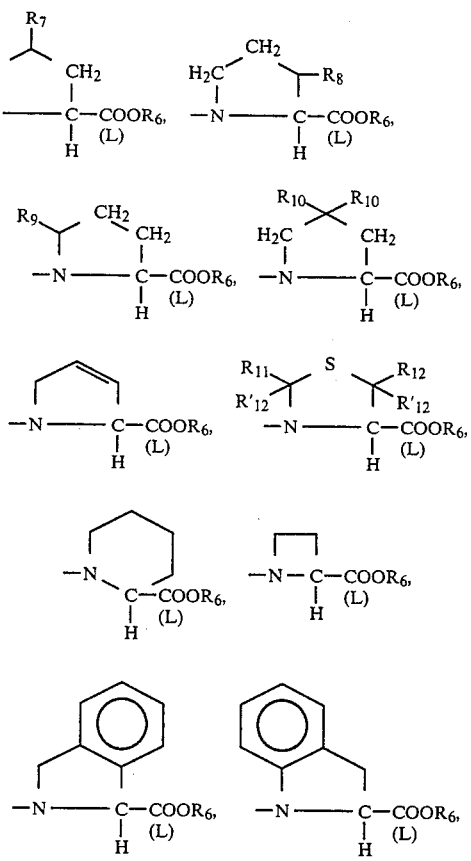

-continued

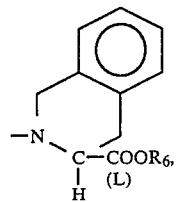

$R_7$ is hydrogen, lower alkyl, halogen, keto, hydroxy,

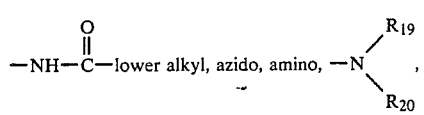

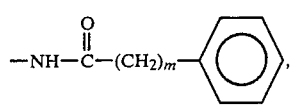

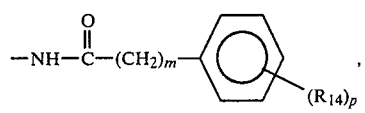

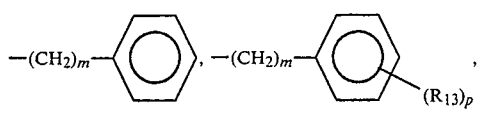

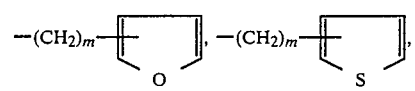

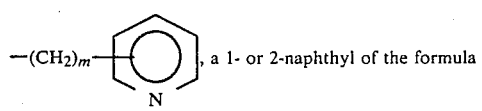

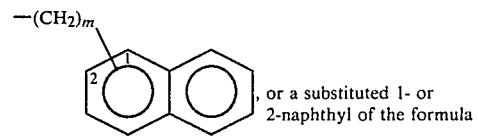

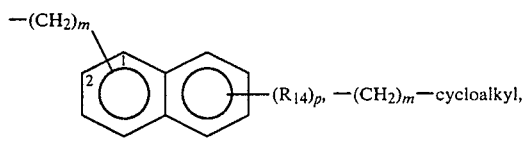

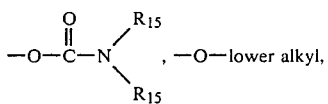

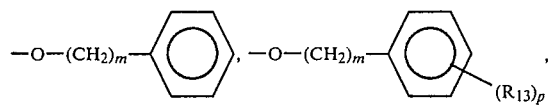

a 1- or 2-naphthyloxy of the formula

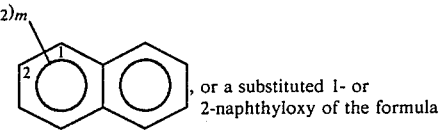, or a substituted 1- or 2-naphthyloxy of the formula

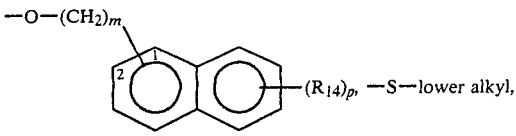, —S—lower alkyl,

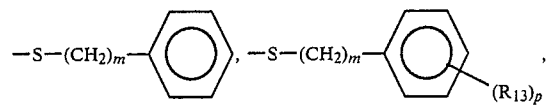

or a 1- or 2-naphthylthio of the formula

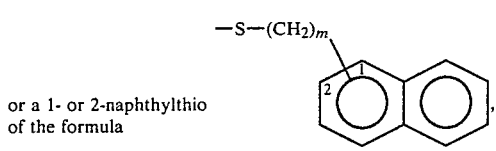, or a substituted 1- or 2-naphthyl-thio of the formula

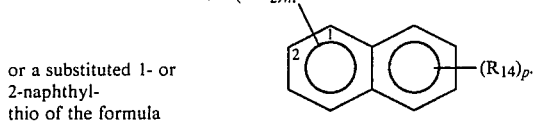

$R_8$ is keto, halogen,

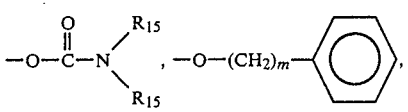, —O—(CH$_2$)$_m$—<phenyl>,

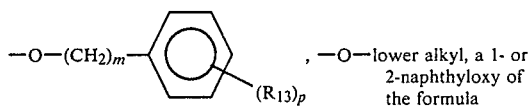, —O—lower alkyl, a 1- or 2-naphthyloxy of the formula

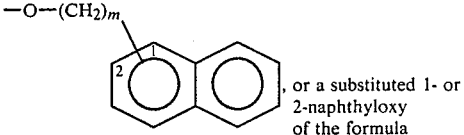, or a substituted 1- or 2-naphthyloxy of the formula

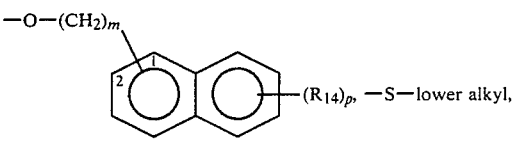, —S—lower alkyl,

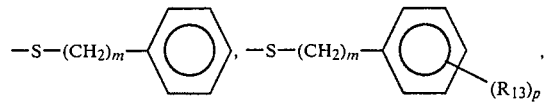

or a 1- or 2-naphthylthio of the formula

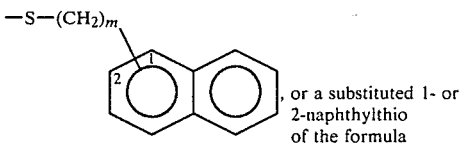, or a substituted 1- or 2-naphthylthio of the formula

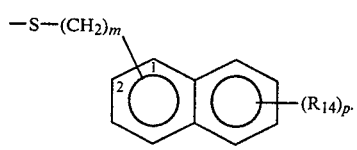

R$_9$ is keto

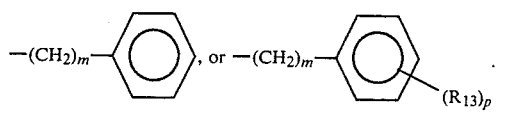

R$_{10}$ is halogen or —Y—R$_{16}$.
R$_{11}$, R$_{11}'$, R$_{12}$ and R$_{12}'$ are independently selected from hydrogen and lower alkyl or R$_{11}'$, R$_{12}$ and R$_{12}'$ are hydrogen and R$_{11}$ is phenyl or

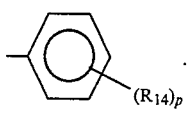

R$_{13}$ is lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio or phenylmethyl.

R$_{14}$ is lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one, two, three, or four.

p is one, two or three provided that p is more than one only if R$_{13}$ or R$_{14}$ is methyl, methoxy, chloro, or fluoro.

R$_{15}$ is hydrogen or lower alkyl of 1 to 4 carbons.

Y is oxygen or sulfur.

R$_{16}$ is lower alkyl of 1 to 4 carbons,

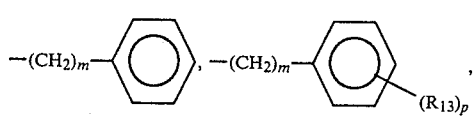

or the R$_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

R$_5$ is hydrogen, lower alkyl,

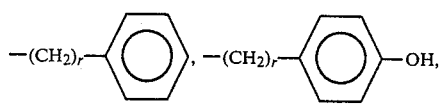

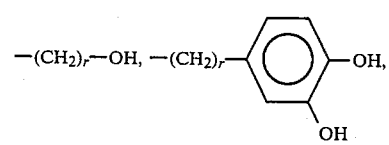

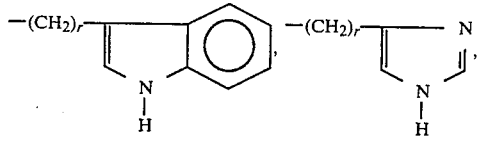

—(CH$_2$)$_r$—NH$_2$, —(CH$_2$)$_r$—SH, —(CH$_2$)$_r$—S—lower alkyl,

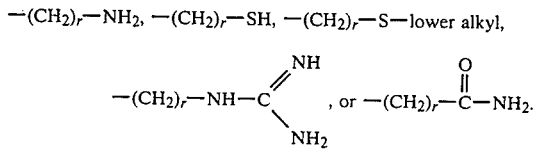

r is an integer from 1 to 4.
R$_{19}$ is lower alkyl, benzyl, or phenethyl.
R$_{20}$ is hydrogen, lower alkyl, benzyl or phenethyl.
n is one or two.

R$_1$ is hydrogen, lower alkyl, halo substituted lower alkyl,

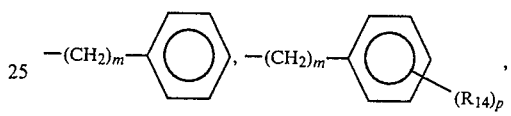

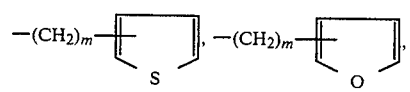

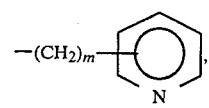

—(CH$_2$)$_m$—cycloalkyl, or —(CH$_2$)$_r$—NH$_2$.

R$_2$ is lower alkyl, 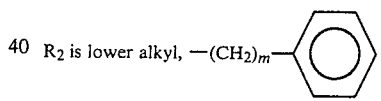

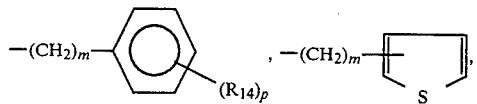

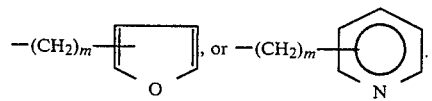

R$_3$ is lower alkyl, 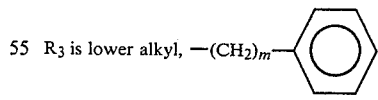

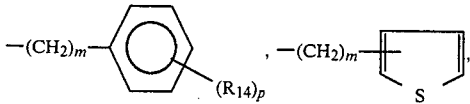

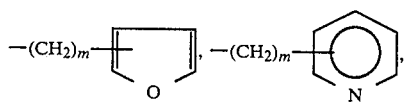

halo substituted lower alkyl, —(CH$_2$)$_m$—cycloalkyl,

-continued

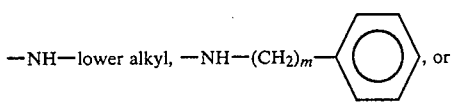

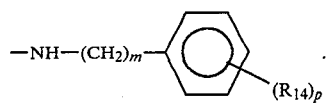

$R_6$ is hydrogen, lower alkyl, benzyl, benzhydryl, or

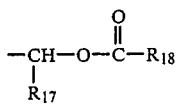

wherein $R_{17}$ is hydrogen, lower alkyl, cycloalkyl or phenyl, and $R_{18}$ is hydrogen, lower alkyl, lower alkoxy, phenyl, or $R_{17}$ and $R_{18}$ taken together are —(CH$_2$)$_2$—, —(CH$_2$)$_3$—, —CH=CH, or

DETAILED DESCRIPTION OF THE INVENTION

This invention is directed to the various novel acyloxyketone substituted amino and imino acid compounds of formula I above, intermediates for preparing such compounds, and compositions and methods of using compositions containing these novel compounds.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The symbols

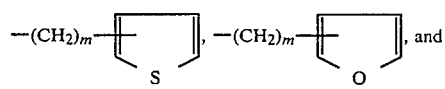

represent that the alkylene bridge is attached to an available carbon atom.

The compounds of formula I can be prepared by coupling a carboxylic acid of the formula

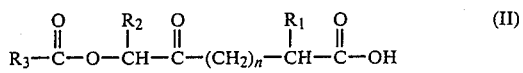

with the amino or imino acid ester of the formula $$HX \qquad\qquad (III)$$

in the presence of a coupling agent such as dicyclohexylcarbodiimide wherein $R_6$ in the definition of X is an easily removable ester protecting group such as benzyl or t-butyl. Removal of the $R_6$ protecting group such as by hydrogenation when $R_6$ is benzyl or treatment with trifluoroacetic acid when $R_6$ is t-butyl yields the products of formula I wherein $R_6$ is hydrogen.

The carboxylic acid intermediate of formula II can be prepared by reacting the acyloxyketone of the formula

with the Gignard reagent of the formula

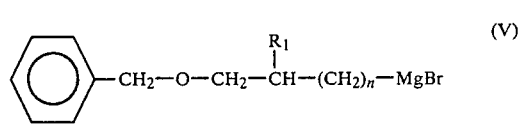

to yield

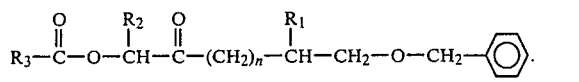

Catalytic hydrogenation of VI yields

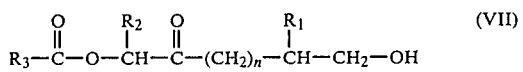

which is oxidized for example by treating with pyridinium dichromate to give the intermediate of formula II.

Alternatively, the acyloxyketone of formula IV can be reacted with the Grignard reagent of the formula

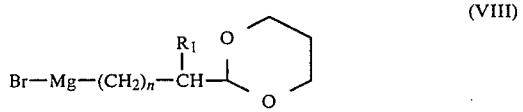

to yield

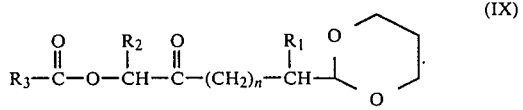

Hydrolysis of IX yields

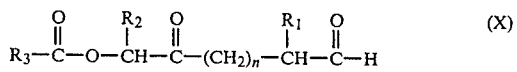 (X)

which is then oxidized for example by treatment with Jones Reagent (chromic anhydride in dilute sulfuric acid) to yield the intermediate of formula II.

The acyloxyketone starting material of formula IV when $R_3$ is other than —NH-lower alkyl

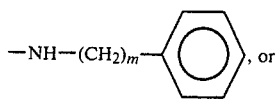, or

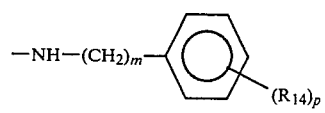

is prepared by acylating a carboxylic acid ester of the formula

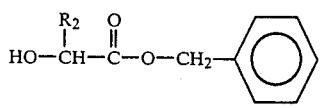 (XI)

with an acid chloride of the formula

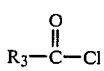 (XII)

in the presence of triethylamine and dimethylaminopyridine to yield

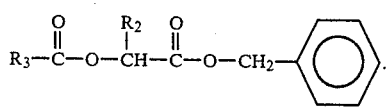 (XIII).

Removal of the benzyl protecting group such as by hydrogenation yields the desired starting material.

When $R_3$ is —NH-lower alkyl

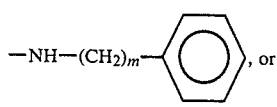, or

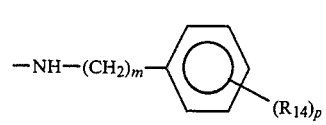

the acyloxyketone of formula IV is prepared by treating the carboxylic acid ester of formula XI with the isocyanate of the formula

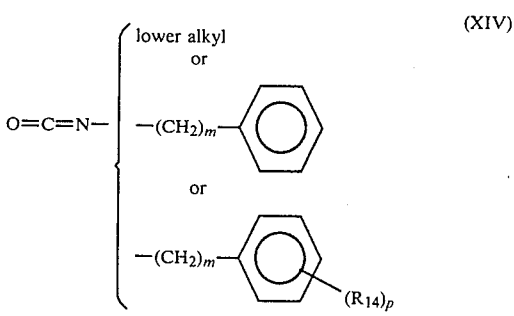 (XIV)

Removal of the benzyl protecting group yields the desired starting material.

In the above reactions if $R_5$ is

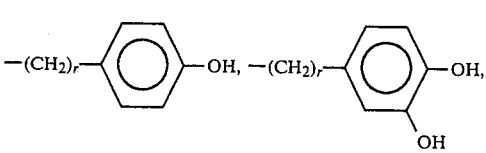

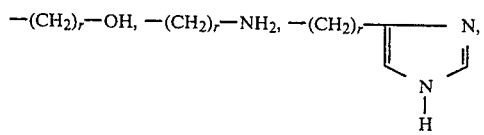

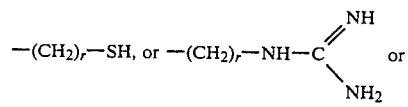

if $R_1$ is —$(CH_2)_r$—$NH_2$ then the hydroxyl, amino, imidazolyl, mercaptan or guanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

The ester products of formula I wherein $R_6$ is lower alkyl, benzyl or benhydryl can be chemically treated such as with sodium hydroxide in aqueous dioxane or with trimethylsilylbromide to yield the products of formula I wherein $R_6$ is hydrogen. The benzyl and benzhydryl esters can also be hydrogenated, for example by treating with hydrogen in the presence of a palladium on carbon catalyst. The ester products of formula I wherein $R_6$ is

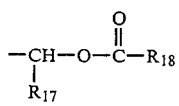

may be obtained by employing the acid chloride of formula III in the above reactions with such ester group already in place. Such ester reactants can be prepared by treating the corresponding amino or imino acid of formula III wherein $R_6$ is hydrogen with an acid chloride such as

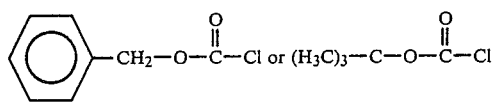

so as to protect the N-atom. The protected amino or imino acid is then reacted in the presence of a base with a compound of the formula

(XV)

wherein L is a leaving group such as chlorine, bromine, tolylsulfonyl, etc., followed by removal of the N-protecting group such as by treatment with acid or hydrogenation.

The ester products of formula I wherein $R_6$ is

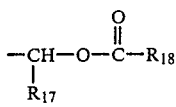

can also be obtained by treating the product of formula I wherein $R_6$ is hydrogen with a molar excess of the compound of formula XV.

The products of formula I wherein $R_7$ is amino may be obtained by reducing the corresponding products of formula I wherein $R_7$ is azido.

Preferred compounds of this invention with respect to the amino or imino acid or ester part of the structure of formula I are those
wherein:
$R_5$ is hydrogen, straight or branched chain lower alkyl of 1 to 4 carbons, $-CH_2-OH$,

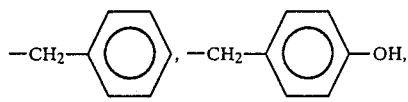

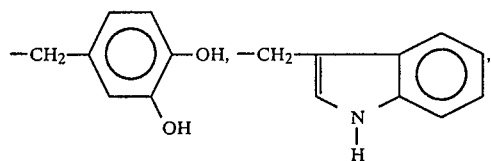

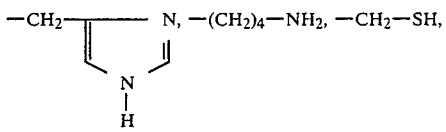

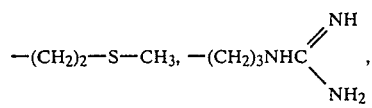

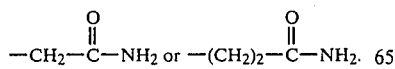

$R_6$ is hydrogen, an alkali metal salt ion, straight or branched chain lower alkyl of 1 to 4 carbons, or

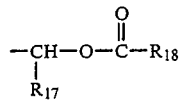

$R_{17}$ is hydrogen, straight or branched chain lower alkyl of 1 to 4 carbons, or cyclohexyl and $R_{18}$ is straight or branched chain lower alkyl of 1 to 4 carbons or phenyl.

$R_7$ is hydrogen.

$R_7$ is hydroxy.

$R_7$ is straight or branched chain lower alkyl of 1 to 4 carbons or cyclohexyl.

$R_7$ is amino.

$R_7$ is —O—lower alkyl wherein lower alkyl is straight or branched chain of 1 to 4 carbons.

$R_7$ is

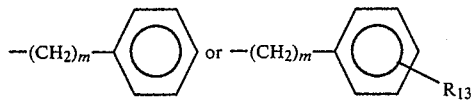

wherein m is zero, one or two and $R_{13}$ is methyl, methoxy, methylthio, chloro, bromo, fluoro, or hydroxy.

$R_7$ is

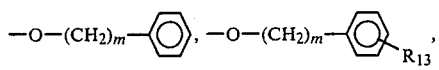

1-naphthyloxy or 2-naphthyloxy wherein m is zero, one, or two and $R_{13}$ is methyl, methoxy, methylthio, chloro, bromo, fluoro, or hydroxy.

$R_7$ is —S—lower alkyl wherein lower alkyl is straight or branched chain of 1 to 4 carbons.

$R_7$ is

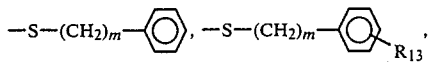

1-naphthylthio, or 2-naphthylthio wherein m is zero, one, or two and $R_{13}$ is methyl, methoxy, methylthio, chloro, bromo, fluoro, or hydroxy.

$R_8$ is —O—lower alkyl wherein lower alkyl is straight or branched chain of 1 to 4 carbons.

$R_8$ is

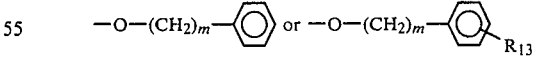

wherein m is zero, one, or two and $R_{13}$ is methyl, methoxy, methylthio, chloro, bromo, fluoro, or hydroxy.

$R_8$ is —S—lower alkyl wherein lower alkyl is straight or branched chain of 1 to 4 carbons.

$R_8$ is

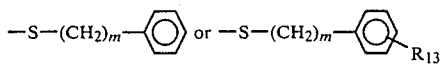

wherein m is zero, one or two and $R_{13}$ is methyl, methoxy, methylthio, chloro, bromo, fluoro or hydroxy.

$R_9$ is phenyl, 2-hydroxyphenyl, or 4-hydroxyphenyl.

$R_{10}$ are both fluoro or chloro.

$R_{10}$ are both —Y—$R_{16}$ wherein Y is O or S, $R_{16}$ is straight or branched chain lower alkyl of 1 to 4 carbons or the $R_{16}$ groups join to complete an unsubstituted 5- or 6-membered ring or said ring in which one or more of the available carbons has a methyl or dimethyl substituent.

$R_{11}$, $R_{11}'$, $R_{12}$ and $R_{12}'$ are all hydrogen, or $R_{11}$ is phenyl, 2-hydroxyphenyl, or 4-hydroxyphenyl and $R_{11}'$, $R_{12}$ and $R_{12}'$ are hydrogen.

Most preferred compounds of this invention with respect to the amino or imino acid or ester part of the structure of formula I are those
wherein:

X is

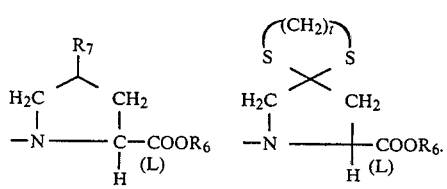

$R_6$ is hydrogen,

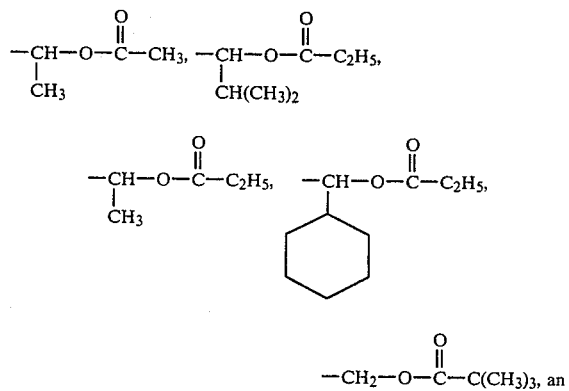

alkali metal salt ion, or —$C_2H_5$.

$R_7$ is hydrogen, cyclohexyl, lower alkoxy of 1 to 4 carbons,

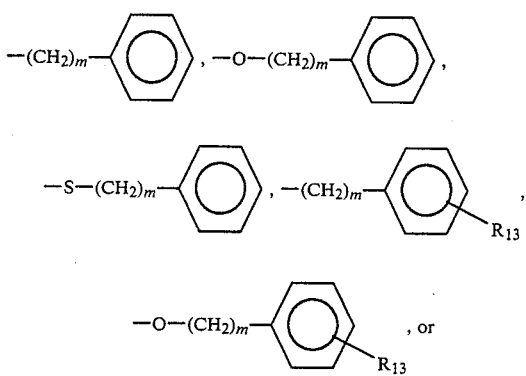

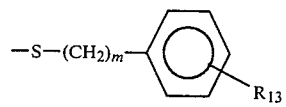

wherein m is zero, one, or two and $R_{13}$ is methyl, methoxy, methylthio, Cl, Br, F, or hydroxy, especially preferred wherein $R_7$ is hydrogen.

t is two or three, especially where t is two.

Preferred compounds of this invention with respect to the acyloxyketone portion of the structure of formula I are those
wherein:

$R_1$ is hydrogen, straight or branched chain lower alkyl of 1 to 4 carbons, —$CF_3$, —$(CH_2)_4$—$NH_2$,

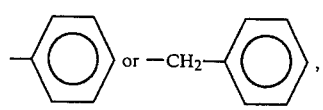

especially hydrogen or methyl.

n is one.

$R_2$ is

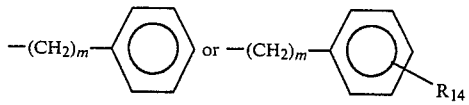

wherein m is zero, one, or two and $R_{14}$ is methyl, methoxy, methylthio, Cl, Br, F, or hydroxy, especially benzyl.

$R_3$ is

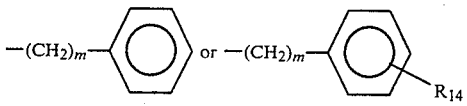

wherein m is zero, one, or two and $R_{14}$ is methyl, methoxy, methylthio, Cl, Br, F, or hydroxy, especially phenyl.

The compounds of formula I wherein $R_6$ is hydrogen form salts with a variety of inorganic or organic bases. The non-toxic, pharmaceutically acceptable salts are preferred, although other salts are also useful in isolating or purifying the product. Such pharmaceutically acceptable salts include alkali metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

As shown above, the amino or imino acid portion of the molecule of the products of formula I is in the L-configuration. An asymmetric center is also present in the acyloxyketone portion of the molecule at the carbon having the $R_2$ substituent and a second asymmetric center is present in the acyloxyketone portion of the molecule when $R_1$ is other than hydrogen. Thus, the compounds of formula I can exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the $R_7$, $R_8$ and $R_9$ substituent in the starting material of formula III.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as teblets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is

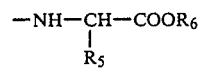

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg. per kilogram per day, produces the desired analgesic activity. The composition is preferably administered orally but parenteral routes such as subcutaneous can also be employed.

The following examples are illustrative of the invention. Temperatures are given in degrees centigrade.

EXAMPLE 1

1-[(5S)-5-(Benzoyloxy)-1,4-dioxo-6-phenylhexyl]-L-proline (a) (S)-α-Hydroxybenzenepropanoic acid To a suspension of L-phenylalanine (100 g., 0.60 mole) in 350 ml. of water is added 600 ml. of 1N hydrochloric acid. The resulting solution is cooled to 0° and 900 ml. of 10% sulfuric acid is added followed by the dropwise addition of a solution of sodium nitrite (90 g.) in 480 ml. of water over a period of two hours. The resulting mixture is stirred at room temperature for 15 hours. The solution is thereafter extracted twice with ether and the organic extracts are dried (MgSO4). The solvent is removed at reduced pressure and the residue treated with benzene to afford a colorless solid which is then recrystallized from hot benzene to give 61.6 g. of (S)-α-hydroxybenzenepropanoic acid as a white crystalline solid; m.p. 123°-125°; $[\alpha]_D^{20} = -26.9$ (c=1.1, acetone).

(b) (S)-α-Hydroxybenzenepropanoic acid, phenyl methyl ester

To a solution of (S)-α-hydroxybenzenepropanoic acid (5.0 g., 0.03 mole) in 50 ml. of dry dimethylformamide under argon is added sodium bicarbonate (5.0 g., 2 eq.), followed by benzyl bromide (3.58 ml., 1 eq.), and the resulting solution is stirred at room temperature for 40 hours. The solution is diluted with water and extracted with ether (3 times). The ether extracts are combined and washed with water, 1N sodium bicarbonate (twice), water and brine. After drying (MgSO4), the solvent is removed at reduced pressure. The residue is flash chromatographed [Whatman silica gel LPS-1; solvent, ether:hexane (3:7)] to give 5.13 g. of (S)-α-hydroxybenzenepropanoic acid, phenylmethyl ester as a pale yellow oil; $R_f = 0.57$ (silica gel, ether).

(c) (S)-α-(Benzoyloxy)benzenepropanoic acid, phenylmethyl ester

A mixture of (S)-α-hydroxybenzenepropanoic acid, phenylmethyl ester (5.1 g., 20 mmole), triethylamine (6.97 ml., 2.5 eq.), dimethylaminopyridine (120 mg., 0.05 eq.) and benzoyl chloride (3.48 ml., 1.5 eq.) in anhydrous dichloromethane (30 ml.) is stirred for 18 hours at room temperature under argon. 1N Sodium bicarbonate (25 ml.) is added to the solution. After one hour, the solution is diluted with dichloromethane and washed with water, 1N hydrochloric acid (twice), 1N sodium bicarbonate (twice), water and brine. After drying (MgSO4), the solvent is removed at reduced pressure. The residue is flash chromatographed [Whatman silica gel LPS-1; solvent, ether:hexane (1:9)] to give 6.35 g. of (S)-α-(benzoyloxy)benzenepropanoic acid, phenylmethyl ester as a colorless oil; $R_f$=0.42 [silica gel, ether:hexane (3:7)].

(d) (S)-α-(Benzoyloxy)benzenepropanoic acid

A mixture of (S)-α-(benzoyloxy)benzenepropanoic acid, phenylmethyl ester (6.35 g., 17.6 mmole), 10% palladium on carbon catalyst (1.2 g.) and ethyl acetate (35 ml.) is stirred under hydrogen gas for 2.5 hours. The solution is filtered (millipore), and the filtrate is concentrated to give 4.75 g. of (S)-α-(benzoyloxy)benzenepropanoic acid as a white solid; $R_f$=0.65 [silica gel, dichloromethane:methanol:acetic acid (18:1:1)].

(e) (S)-2-(Benzoyloxy)-5-(1,3-dioxan-2-yl)-1-phenyl-3-pentanone

To a 0° solution of (S)-α-(benzoyloxy)benzenepropanoic acid (1.6 g., 5.92 mmole) in anhydrous tetrahydrofuran (10 ml.) is added 1,1′-carbonyldiimidazole (1.0 g., 1.05 eq.), and the resulting solution is stirred at 0° for 2 hours under argon.

The solution is cooled to −50° and a Grignard solution prepared from refluxing a mixture of magnesium turnings (0.2 g., 1.3 eq.), anhydrous tetrahydrofuran (10 ml.) and 2-(2-bromoethyl)-1,3-dioxane (1.15 ml., 5.92 mmole) for 20 minutes under argon is added dropwise through a syringe. The resulting mixture is stirred for 30 minutes at −50°. 20 ml. of 10% ammonium chloride solution is added, and the solution is allowed to warm to room temperature. The solution is diluted with ether and the aqueous layer is drained. The organic layer is washed with water, 1N hydrochloric acid, 1N sodium bicarbonate, water and brine. After drying (MgSO4), the solvent is removed at reduced pressure. The residue is flash chromatographed [Whatman silica gel LPS-1; solvent, petroleum ether:ether (2:1)] to give 710 mg. of (S)-2-(benzoyloxy)-5-(1,3-dioxan-2-yl)-1-phenyl-3-pentanone as a white solid; $R_f$=0.62; secondary spot (not UV active) $R_f$=0.51 (silica gel, ether).

(f) (S)-5-(Benzoyloxy)-4-oxo-6-phenylhexanal

A solution of (S)-2-(benzoyloxy)-5-(1,3-dioxan-2-yl)-1-phenyl-3-pentanone (300 mg., 0.8 mmole), acetone (15 ml.) and p-toluenesulfonic acid monohydrate (20 mg.) is stirred at reflux under argon for 75 minutes. Propionaldehyde (1 ml.) is added and the solution gradually darkens. After 30 minutes another 1 ml. of propionaldehyde is added and the solution is refluxed for 45 minutes. The solution is diluted with ether and washed with water, 1N sodium bicarbonate and brine. After drying (MgSO4), the solvent is removed at reduced pressure. The residue is flash chromatographed [Whatman silica gel LPS-1, solvent, hexane:acetone (82:18), 25×280 nm. column, approximately 13 ml. fractions collected] to give 180 mg. of (S)-5-(benzoyloxy)-4-oxo-6-phenylhexanal as a colorless oil; $R_f$=0.52 [silica gel, hexane:acetone (1:1)].

(g) (S)-5-(Benzoyloxy)-4-oxo-6-phenylhexanoic acid

A 0° solution of (S)-5-(benzoyloxy)-4-oxo-6-phenylhexanal (180 mg., 0.6 mmole) in acetone (10 ml.) is treated with 2 ml. of Jones Reagent (26.72 g. of chromic anhydride, 23 ml. of sulfuric acid, diluted to 100 ml. with water). The resulting solution is stirred for 20 minutes at 0° followed by 20 minutes at room temperature. Several ml. of isopropanol are added and the solution becomes bluish-green. This is diluted with ether. The aqueous layer is drained and extracted with ether. The organic fractions are combined and washed with water (twice). After drying (MgSO4), the solvent is removed at reduced pressure to give 200 mg. of (S)-5-(benzoyloxy)-4-oxo-6-phenylhexanoic acid; $R_f$=0.72 [silica gel, ethyl acetate:pyridine:acetic acid:water (100:20:6:11)].

(h) 1-[(5S)-5-(Benzoyloxy)-1,4-dioxo-6-phenylhexyl]-L-proline, phenylmethyl ester To a 0° solution of (S)-5-(benzoyloxy)-4-oxo-6-phenylhexanoic acid (200 mg., 0.612 mmole), L-proline, phenylmethyl ester, hydrochloride (148 ml., 1 eq.), hydroxybenzotriazole (83 mg., 1 eq.) and diisopropylethylamine (0.128 ml., 1.2 eq.) in anhydrous tetrahydrofuran (6.5 ml.) under argon is added a solution N,N′-dicyclohexylcarbodiimide (126 mg., 1 eq.) in tetrahydrofuran (0.8 ml.). The resulting solution is stirred for one hour at 0° followed by 20 hours at room temperature. The solution is diluted with ether and filtered to remove dicyclohexylurea. The filtrate is washed with 1N hydrochloric acid (twice), 1N sodium bicarbonate (twice), and brine. After drying (MgSO4), the solvent is removed at reduced pressure. The residue is filtered through glass wool using ether to remove additional dicyclohexylurea, and then the material is flash chromatographed [Whatman silica gel LPS-1, solvent, hexane:acetone (75:25); column loaded with the aid of benzene, 25×260 mm. column, approximately 13 ml. fractions collected] to give 250 mg. of 1-[(5S)-5-(benzoyloxy)-1,4-dioxo-6-phenylhexyl]-L-proline, phenylmethyl ester as a colorless oil; $R_f$=0.24 (silica gel, ether).

(i) 1-[(5S)-5-(Benzyloxy)-1,4-dioxo-6-phenylhexyl]-L-proline

A mixture of 1-[(5S)-5-(benzoyloxy)-1,4-dioxo-6-phenylhexyl]-L-proline (250 mg., 0.5 mmole), 10% palladium on carbon catalyst (50 mg.), and ethyl acetate (10 ml.) is stirred under hydrogen gas for 7.5 hours. The solution is filtered (millipore), and the solvent removed at reduced pressure. Ether is added to the residue and crystals form. The solution is filtered to give the desired product as a white hygroscopic solid which is dried under vacuum over $P_2O_5$ to give 150 mg. of 1-[(5S)-5-(benzoyloxy)-1,4-dioxo-6-phenylhexyl]-L-proline; $R_f$=0.40 [silica gel, ethyl acetate:pyridine:acetic acid:water (100:20:6:11)]; m.p. 114°–115°; $[α]_D^{20}$=−112° (c=1.17, pyridine).

Anal. calc'd. for $C_{24}H_{25}NO_6 \cdot 0.17H_2O$: C, 67.59; H, 5.99; N, 3.29. Found: C, 67.59; H, 5.99; N, 3.35.

EXAMPLE 2

1-[(5S,2R)-5-(Benzoyloxy)-2-methyl-1,4-dioxo-6-phenylhexyl]-L-proline (a) 3-Benzyloxy-2-methylpropionitrile Benzyl alcohol (108 g., 1 mole) under argon is treated with 0.3 g. of 60% sodium hydride-mineral oil dispersion. Methacrylonitrile (415 ml., 5 mole) is added dropwise to this solution over a 45 minute period. After the addition is complete, the mixture is heated at 60°–65°. After 12 hours an additional 0.2 g. of 60% sodium hydride-mineral oil dispersion is added. The mixture is then heated for an additional 24 hours, cooled, and acidified with 0.5M citric acid. The bulk of excess methacrylonitrile is removed at reduced pressure on a rotavap. The residue is dissolved in ether and the resulting solution is washed successively with water, 1N hydrochloric acid (twice), 1N sodium bicarbonate (twice), and brine. After drying (MgSO$_4$), the solvent is removed at reduced pressure and the residue distilled to give 109.5 g. of 3-benzyloxy-2-methylpropionitrile as a colorless liquid; b.p. 83°–86° (0.1 mm. Hg.); R$_f$=0.44 [silica gel, hexane:ether (4:6)].

(b) 3-Benzyloxy-2-methylpropanoic acid, methyl ester

A solution of 3-benzyloxy-2-methylpropionitrile (108.65 g., 0.62 mole) in methanol (540 ml.) is cooled to between −10° and −5° and stirred while hydrochloric acid gas is bubbled in. After the solution becomes saturated with hydrochloric acid, it is refluxed for 2.25 hours and allowed to cool. The solution is filtered, and the filtrate is concentrated at reduced pressure. The residue is taken up in 1N sodium bicarbonate and extracted twice with ether. After drying (MgSO$_4$), the solvent is removed at reduced pressure to give a pale yellow liquid. This is distilled to give 65.25 g. of 3-benzyloxy-2-methylpropanoic acid, methyl ester as a colorless liquid; b.p. 100°–102° (0.08 mm Hg.); R$_f$=0.69 (silica gel, ether).

(c) 3-Benzyloxy-2-methyl-1-propanol

To a stirred suspension of lithium aluminum hydride (8.92 g., 0.75 eq.) in 100 ml. of anhydrous ether at 0° under argon is added 3-benzyloxy-2-methylpropanoic acid, methyl ester (65.25 g., 0.313 mole) in 100 ml. of ether dropwise over a period of one hour. After 18 hours, the solution is cooled to 0°. Excess lithium aluminum hydride is decomposed by the addition of 9 ml. of water, 9 ml. of 15% aqueous sodium hydroxide, and 27 ml. of water in succession. The solution is stirred vigorously for 15 minutes and then filtered. The filtrate is dried (MgSO$_4$) and concentrated at reduced pressure to give 52.79 g. of 3-benzyloxy-2-methyl-1-propanol as a colorless liquid; R$_f$=0.49 (silica gel, ether).

(d) 3-Benzyloxy-2-methyl-1-bromopropane

To a −10° solution of 3-benzyloxy-2-methyl-1-propanol (26.4 g., 0.146 mole) and diisopropylethylamine in anhydrous dichloromethane (350 ml.) is added dropwise methylsulfonylchloride (12.46 ml., 1.1 eq.) over a period of 10 minutes. The resulting solution is stirred for 40 minutes at −10°. The solution is diluted with additional dichloromethane and washed with water, 1N hydrochloric acid (twice), 1N sodium bicarbonate and brine. After drying (MgSO$_4$), the solvent is removed at reduced pressure to give a bright yellow liquid; R$_f$=0.58 (silica gel, ether). This is dissolved in 300 ml. of acetone. Lithium bromide (31.92 g., 3 eq.) is added, and the solution is refluxed under argon for 4 hours. The solution is filtered and the filtrate is concentrated. The residue is dissolved in ether and washed with water (twice), 1N sodium bicarbonate (twice), and brine. After drying (MgSO$_4$), the solvent is removed at reduced pressure.

An additional 26.4 g. of 3-benzyloxy-2-methyl-1-propanol is treated as described above.

The two batches of crude bromide are combined and chromatographed [Waters Prep liquid chromatography System 500, solvent; hexane:dichloromethane (19:1)] and Kugelrohr distilled to give 62.9 g. of 3-benzyloxy-2-methyl-1-bromopropane as a colorless liquid; b.p. 145°–148° (0.08 mm of Hg.); R$_f$=0.75 (silica gel, ether).

(e) 3-Benzyloxy-2-methyl-1-propylmagnesium bromide

A mixture of 3-benzyloxy-2-methyl-1-bromopropane (3.35 g., 13.8 mmole) and magnesium turnings (0.58 g., 23.8 mmole) in anhydrous tetrahydrofuran (25 ml.) under argon is irradiated at room temperature with an ultrasonic cleaner for 2.25 hours to give 3-benzyloxy-2-methyl-1-propylmagnesium bromide.

(f) (2S)-2-Benzoyloxy-6-benzyloxy-5-methyl-1-phenylhexan-3-one

To a solution of (S)-α-(benzoyloxy)benzenepropanoic acid (1.24 g., 4.58 mmole), prepared as set forth in Example 1(d), in anhydrous tetrahydrofuran (20 ml.) under argon is added 1,1′-carbonyldiimidazole (0.78 g., 4.81 mmole). After stirring at room temperature for 2 hours, the solution is cooled to −35°. To this solution is added dropwise over 15 minutes the solution of 3-benzyloxy-2-methyl-1-propylmagnesium bromide in anhydrous tetrahydrofuran prepared in step (e). After stirring at −35° for one hour, the reaction is quenched with 10% ammonium chloride (35 ml.). The resulting mixture is diluted with ether and then washed successively with water (twice), 1N hydrochloric acid, 1N sodium bicarbonate, and brine. After drying (MgSO$_4$), the solvent is removed at reduced pressure and the residue flash chromatographed [Whatman silica gel LPS-1, solvent; hexane:acetone (95:5)] to give 1.52 g. of (2S)-2-benzoyloxy-6-benzyloxy-5-methyl-1-phenylhexan-3-one as a nearly colorless oil; R$_f$=0.31 [silica gel, hexane:ethyl acetate (4:1)].

(g) (2S)-2-Benzoyloxy-6-hydroxy-5-methyl-1-phenylhexan-3-one

A mixture of (2S)-2-benzoyloxy-6-benzyloxy-5-methyl-1-phenylhexan-3-one (1.52 g., 3.65 mmole), palladium hydroxide on carbon catalyst (320 mg.) and acetic acid (0.3 ml.) in 100 ml. of ethyl acetate is stirred under hydrogen gas for 3.5 hours. The solution is filtered (millipore). The filtrate is diluted with additional ethyl acetate and washed twice with 1N sodium bicarbonate. After drying (MgSO$_4$), the solvent is removed under reduced pressure. The residue is flash chromatographed [Whatman silica gel LPS-1; solvent, hexane:ethyl acetate (4:1)] to give 930 mg. of (2S)-2-benzoyloxy-6-hydroxy-5-methyl-1-phenylhexan-3-one as a colorless oil; R$_f$=0.18 [silica gel, hexane:ethyl acetate (4:1)].

(h) (5S)-5-Benzoyloxy-2-methyl-4-oxo-6-phenylhexanoic acid

To a solution of (2S)-2-benzoyloxy-6-hydroxy-5-methyl-1-phenylhexan-3-one (930 mg., 2.8 mmole) in anhydrous dimethylformamide (15 ml.) under argon is added pyridinium dichromate (3.47 g., 3.5 eq.). The resulting mixture is stirred at room temperature for 18 hours and then diluted with water (approximately 100 ml.). The resulting solution is extracted with ether (2×100 ml.). The organic fractions are combined and washed with water (twice), 1N hydrochloric acid (twice), and brine. After drying (MgSO4), the solvent is removed at reduced pressure to give crude product as a pale yellow oil.

This crude product is dissolved in ether and treated with an ether solution of adamantanamine. The resulting amine salt is collected by filtration and washed with ether.

The amine salt is added to ether and the resulting mixture is washed with 1N hydrochloric acid (twice) and brine. After drying (MgSO4), the solvent is removed at reduced pressure to give 740 mg. of (5S)-5-benzoyloxy-2-methyl-4-oxo-6-phenylhexanoic acid as a colorless oil; $R_f=0.17$ [silica gel, hexane:acetone (7:3)].

(i)
1-[(5S,2R)-5-(Benzoyloxy)-2-methyl-1,4-dioxo-6-phenylhexyl]-L-proline, phenylmethyl ester To a solution of (5S)-5-benzoyloxy-2-methyl-4-oxo-6-phenylhexanoic acid (740 mg., 2.17 mmole), L-proline, phenylmethyl ester, hydrochloride (525 mg., 2.17 mmole), 1-hydroxybenzotriazole hydrate (300 mg., 2.21 mmole), and diisopropylethylamine (0.45 ml., 2.6 mmole) in anhydrous tetrahydrofuran (8 ml.) at 0° under argon is added dropwise a solution of dicyclohexylcarbodiimide (457 mg., 2.21 mmole) in tetrahydrofuran (1.5 ml.). The resulting mixture is stirred at 0° for one hour and then warmed to room temperature. After stirring for 16 hours, the mixture is diluted with ether and washed with water, 1N hydrochloric acid (twice), 1N sodium bicarbonate, and brine. After drying (MgSO4), the solvent is removed at reduced pressure to give the desired product as a mixture of diastereomers. Flash chromatography [Whatman silica gel LPS-1; solvent, hexane:dichloromethane:ethyl acetate (6:2:2)] gives 460 mg. of 1-[(5S,2R)-5-(benzoyloxy)-2-methyl-1,4-dioxo-6-phenylhexyl]-L-proline, phenylmethyl ester; $R_f=0.45$ [silica gel, dichloromethane:ethyl acetate:hexane (4:3:3)].

(j)
1-[(5S,2R)-5-(Benzoyloxy)-2-methyl-1,4-dioxo-6-phenylhexyl]-L-proline

A mixture of 1-[(5S,2R)-5-(benzoyloxy)-2-methyl-1,4-dioxo-6-phenylhexyl]-L-proline, phenylmethyl ester (230 mg., 0.435 mmole) and 10% palladium on carbon catalyst (50 mg.) in ethyl acetate (15 ml.) is stirred under hydrogen gas for 4 hours. The resulting mixture is filtered (millipore) and the filtrate concentrated to give the desired product as a colorless solid which is then dried under vacuum over $P_2O_5$ to give 144 mg. of 1-[(5S,2R)-5-(benzoyloxy)-2-methyl-1,4-dioxo-6-phenylhexyl]-L-proline; m.p. 130°–134°; $[\alpha]_D^{20}=-110°$ (c=1.09, pyridine); $R_f=0.37$ [silica gel, ethyl acetate:pyridine:acetic acid; water (180:20:6:11)].

Anal. calc'd. for $C_{25}H_{27}NO_6$: C, 68.63; H, 6.22; N, 3.20. Found: C, 68.77; H, 6.21; N, 3.08.

EXAMPLES 3–61

The carboxylic acid ester shown in Col. I is reacted with the acid chloride shown in Col. II when $R_3$ is other than a substituted amine or the isocyanate shown in Col. III to yield the intermediate of Col. IV. Removal of the benzyl protecting group, treatment with a Grignard reagent followed by hydrogenation or hydrolysis, and then oxidation yields the acyloxyketonecarboxylic acid of Col. V. Coupling the acid of Col. V with the amino or imino acid ester of Col. VI yields the ester product of Col. VII. Removal of the $R_6$ ester group yields the final product wherein $R_6$ is hydrogen.

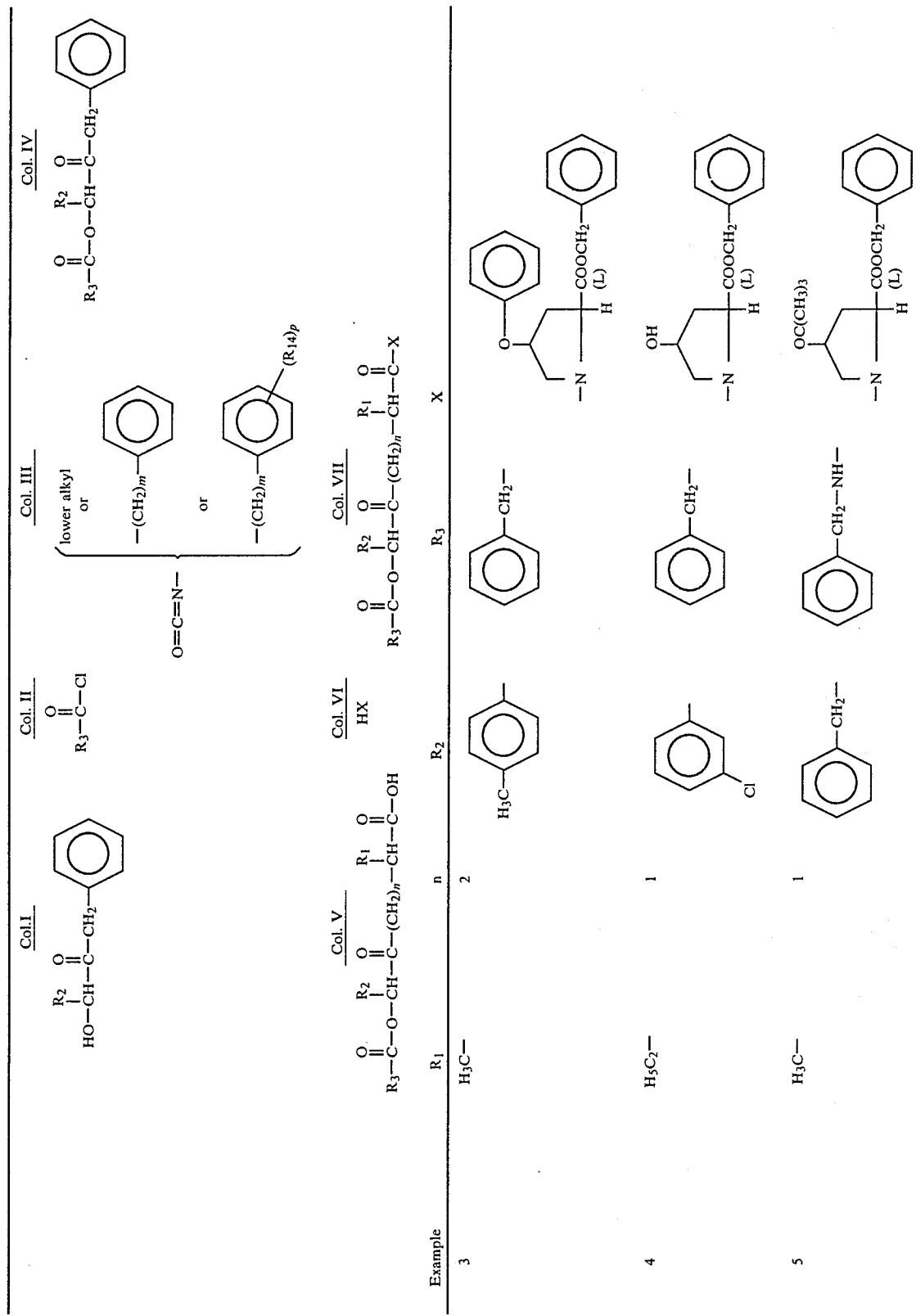

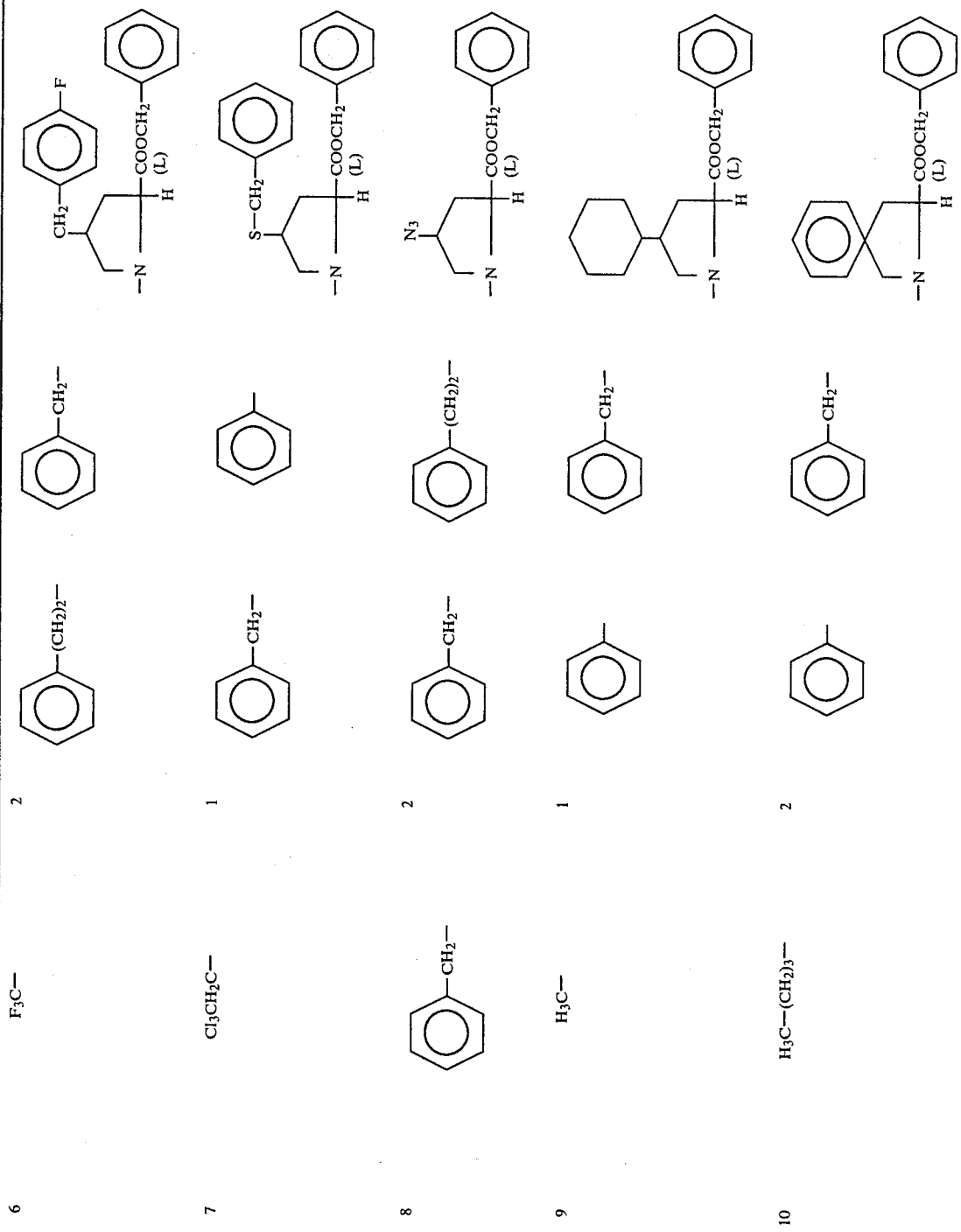

| | | | | |
|---|---|---|---|---|
| 11 | H₅C₂— | thiophene | ⟨C₆H₅⟩CH₂— | -N-CH₂-C(F)(F)-CH(COOCH₂C₆H₅)(H) (L) |
| 12 | H— | furan-CH₂— | ⟨C₆H₅⟩(CH₂)₂— | -N-CH₂-C(OCH₃)(OCH₃)-CH(COOCH₂C₆H₅)(H) (L) |
| 13 | H₃C—(CH₂)₂— | pyridine | ⟨C₆H₅⟩CH₂— | -N-CH₂-C(OCH₂CH₂O)-CH(COOCH₂C₆H₅)(H) (L) |
| 14 | H₃C— | ⟨C₆H₅⟩ | ⟨C₆H₅⟩CH₂— | -N-CH₂-C(SCH₂CH₂S)-CH(COOCH₂C₆H₅)(H) (L) |
| 15 | F₃C— | 4-H₃CO-⟨C₆H₄⟩ | 4-F-⟨C₆H₄⟩CH₂— | -N-CH₂-C(SCH₂CH₂S)-CH(COOCH₂C₆H₅)(H) (L) |

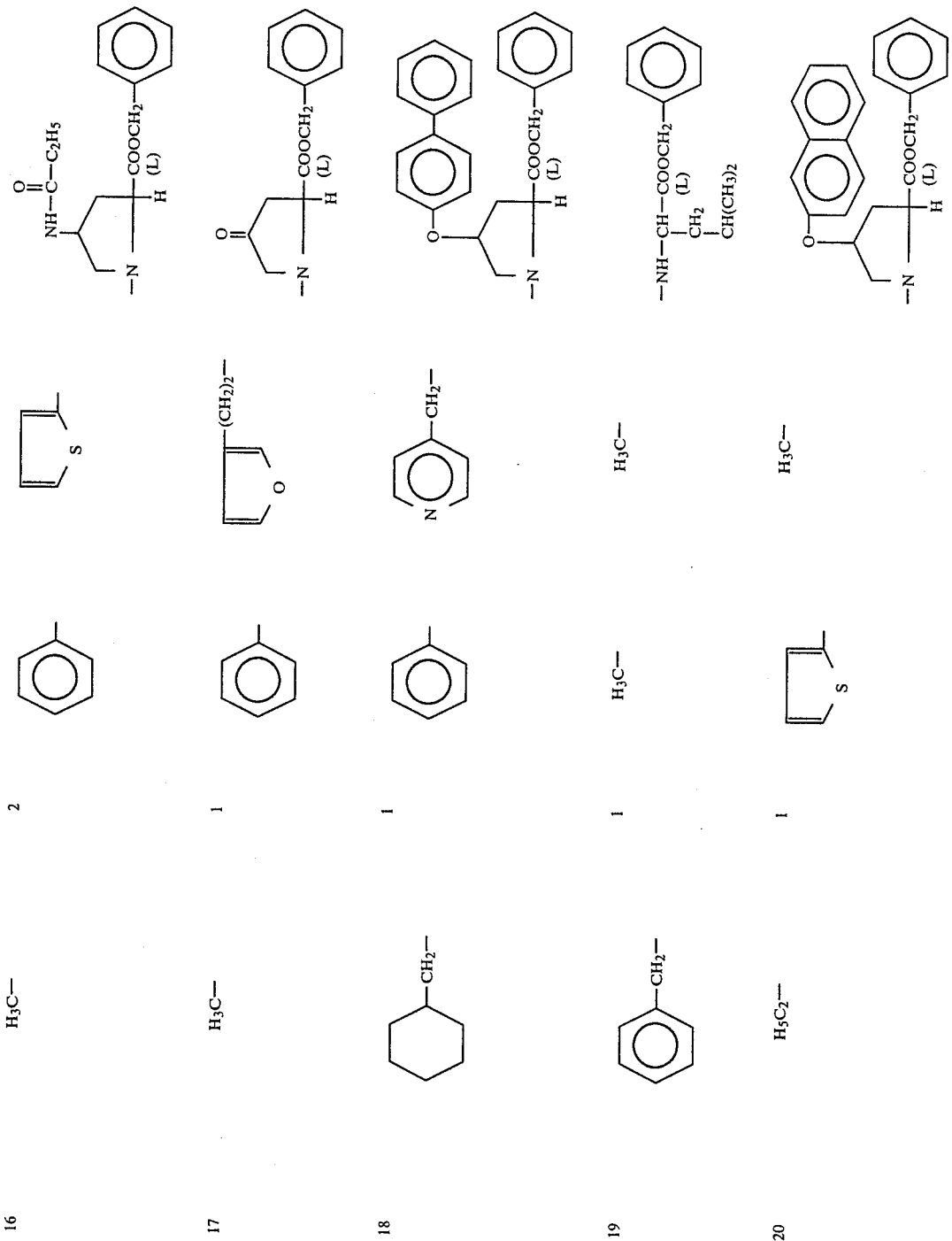

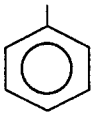

-continued
| | | | |
|---|---|---|---|
| 27 | H₃C— | 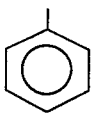 | 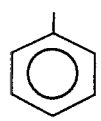 |  |
| 28 | H₃C— | 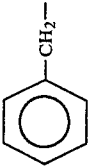 |  |  |
| 29 | H₃C— |  |  |  |
| 30 | H₅C₂— | 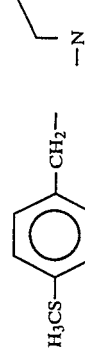 |  |  |
| 31 | H₃C |  |  |  |
| 32 | H₅C₂— |  |  |  |

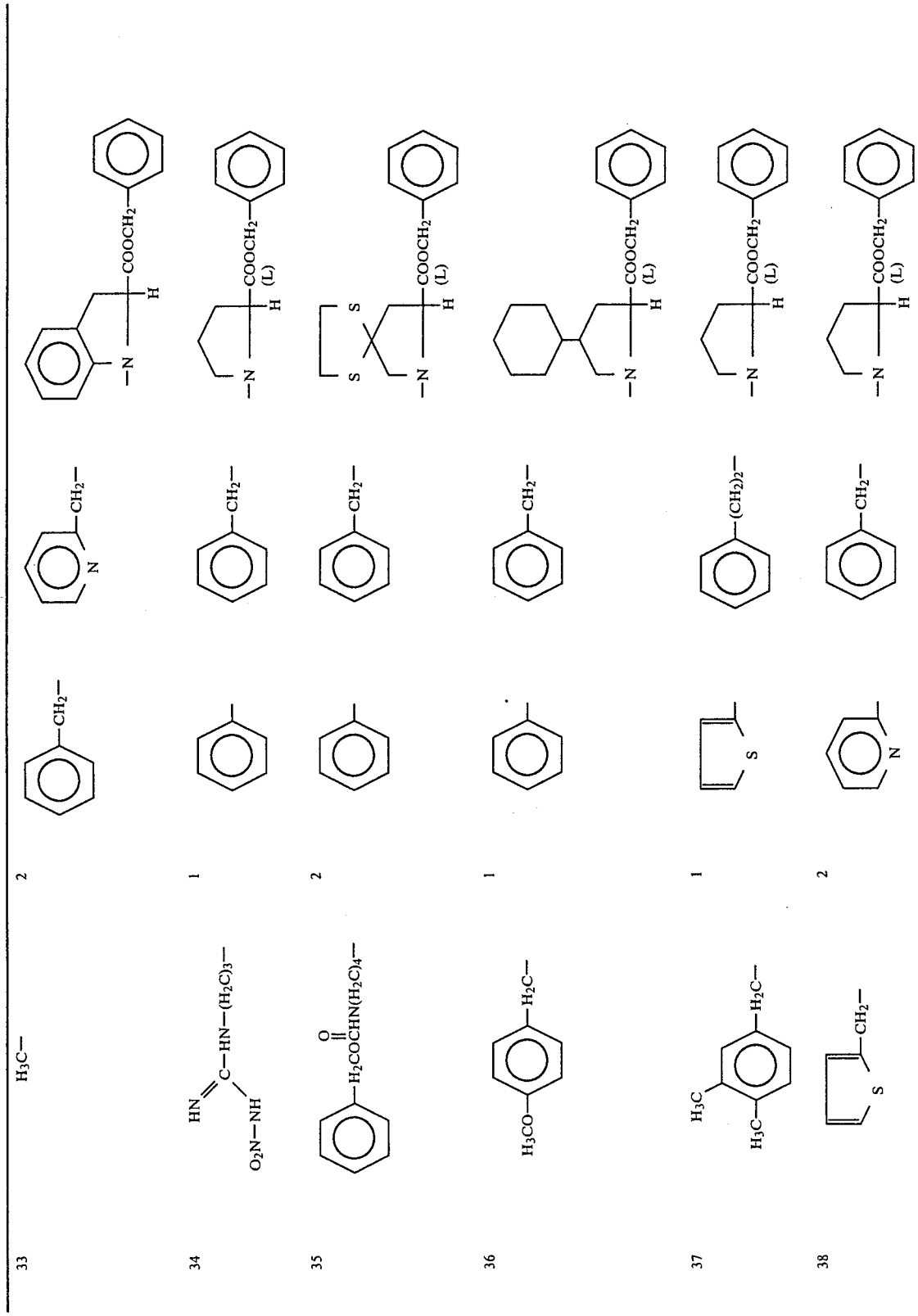

| | | | | |
|---|---|---|---|---|
| 39 | 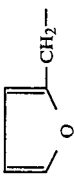 | 1 | 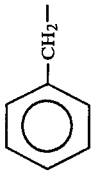 | H₃C—NH— 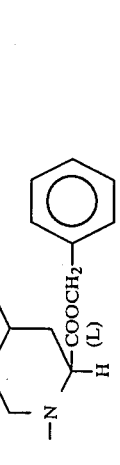 |
| 40 |  | 1 | 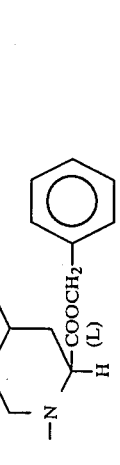 | H₅C₂—NH— 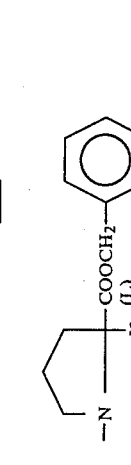 |
| 41 | H₃C— | 1 | 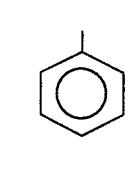 | 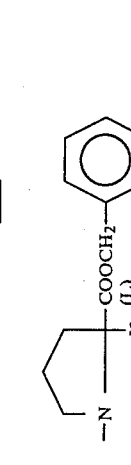 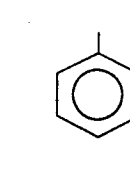 |
| 42 | H₃C— | 1 | 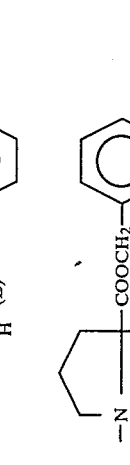 | 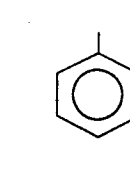 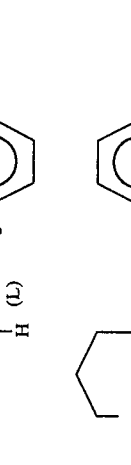 |
| 43 | H₃C— | 1 | 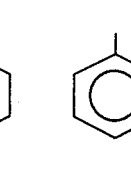 | F₃C—CH₂— 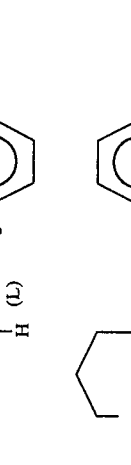 |
| 44 | H₃C— | 1 |  | 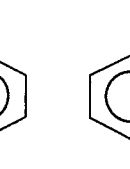 —NH—CH₂—COOCH₂  |
| 45 | F₃C— | 2 | 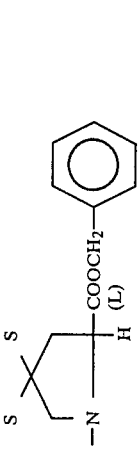 | 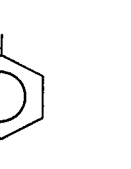 —NH—CH—COOH₂ (L) 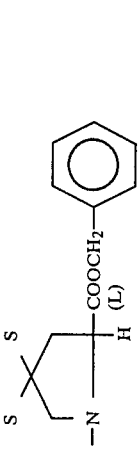 |

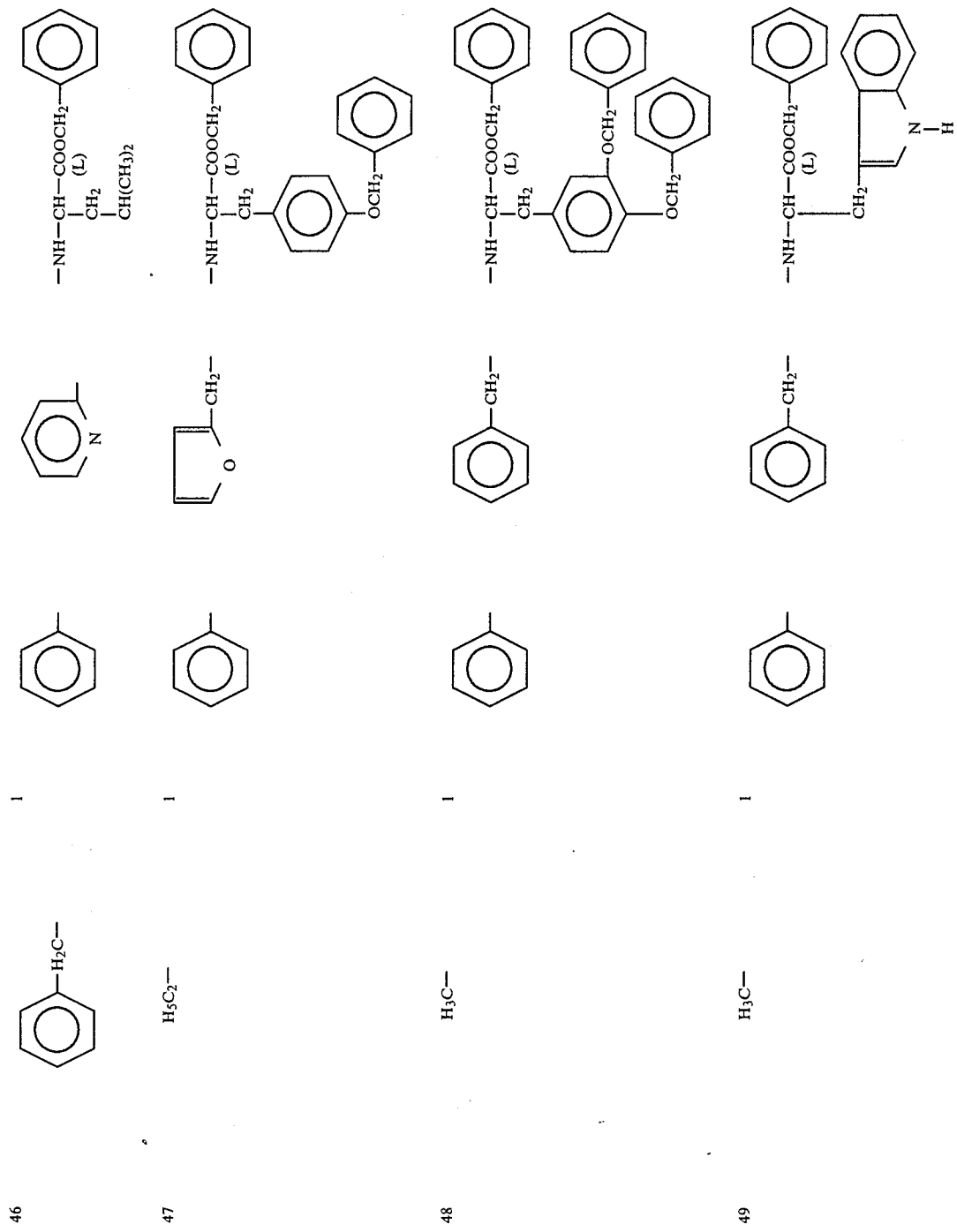

-continued

| | | | |
|---|---|---|---|
| 50 | H₂C—⌬ | ⌬ | ⌬—CH₂— (pyridine-2-yl) | —NH—CH—COOCH₂—⌬ (L) \| CH₂ \| N=⌬—N—CH₂—⌬ |
| 51 | H₃C— | ⌬ | H₃C—(H₂C)₅— | —NH—CH—COOCH₂—⌬ (L) \| (CH₂)₄—NHCOCH₂—⌬ \|\| O |
| 52 | H₃C— | ⌬ | thien-2-yl (⟨S⟩) | —NH—CH—COOCH₂—⌬ (L) \| CH₂—S—CH₂—⌬ |
| 53 | H₅C₂— | ⌬—CH₂— | ⌬—CH₂— | —NH—CH—COOCH₂—⌬ (L) \| (CH₂)₃NHC(=NH)NHNO₂ |
| 54 | H₃C— | ⌬ | ⌬—CH₂— | —NH—CH—COOCH₂—⌬ (L) \| (CH₂)₂—C(=O)—NH₂ |

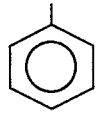

-continued
| 61 | H₃C— | 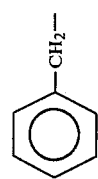 | 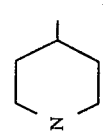 | 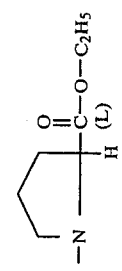 |

The R₁ protecting groups shown in Examples 34, 35 and 40 and the R₅ protecting groups shown in Examples 47, 48, and 50 to 53 are removed as the last step in the synthesis. The R₆ ester groups shown in Examples 55 to 61 are not removed.

EXAMPLE 62

1-[(5S,2R)-5-(Benzoyloxy)-2-methyl-1,4-dioxo-6-phenylhexyl]-L-proline, sodium salt 1-[(5S,2R)-5-(Benzoyloxy)-2-methyl-1,4-dioxo-6-phenylhexyl]-L-proline (1 mmole) is dissolved in water (50 ml.). Aqueous sodium bicarbonate (0.1N, 20 ml.) is added and the aqueous solution is lyophilized. It is then dissolved in water (10 ml.) and applied on a column (5 cm.×60 cm.) of Sephadex chromatography gel G-10 and eluted with water. Fractions containing the desired product are pooled and lyophilized to obtain 1-[(5S,2R)-5-(benzoyloxy)-2-methyl-1,4-dioxo-6-phenylhexyl]-L-proline, sodium salt.

In a similar manner sodium or potassium salts of any of Examples 1 and 3–61 can be prepared.

EXAMPLE 63

1000 tablets each containing the following ingredients:

| | |
|---|---|
| 1-[(5S,2R)-5-(Benzoyloxy)-2-methyl-1,4-dioxo-6-phenylhexyl]-L-proline, sodium salt | 100 mg. |
| Corn starch | 50 mg. |
| Gelatin | 7.5 mg. |
| Avicel (microcrystalline cellulose) | 25 mg. |
| Magnesium stearate | 2.5 mg. | are prepared from sufficient bulk quantities by mixing the 1-[(5S,2R)-5-(benzoyloxy)-2-methyl-1,4-dioxo-6-phenylhexyl]-L-proline, sodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 1 to 61 can be prepared.

A similar procedure can be employed to form tablets containing 50 mg. of active ingredient.

EXAMPLE 64

Two piece #1 gelatin capsules each containing 50 mg. of 1-[(5S)-5-(Benzoyloxy)-1,4-dioxo-6-phenylhexyl]-L-proline, sodium salt are filled with a mixture of the following ingredients:

| | |
|---|---|
| 1-[(5S)-5-(Benzolyoxy)-1,4-dioxo-6-phenylhexyl]-L-proline, sodium salt | 50 mg. |
| Magnesium stearate | 7 mg. |
| Lactose | 193 mg. |
| | 250 mg. |

In a similar manner capsules containing 50 mg. of the product of any of Examples 2 to 62 can be prepared.

EXAMPLE 65

An injectable solution is prepared as follows:

| | |
|---|---|
| 1-[(5S,2R)-5-(Benzoyloxy)-2-methyl-1,4-dioxo-6-phenylhexyl]-L-proline, sodium salt | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and asceptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredients per ml. of solution can be prepared for the product of any of Examples 1 to 61.

EXAMPLE 66

1000 tablets each containing the following ingredients:

| | |
|---|---|
| 1-[(5S,2R)-5-(Benzoyloxy)-2-methyl-1,4-dioxo-6-phenylhexyl]-L-proline, sodium salt | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficient bulk quantities by slugging the 1-[(5S,2R)-5-(benzoyloxy)-2-methyl-1,4-dioxo-6-phenylhexyl]-L-proline, sodium salt, Avicel and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 to 61.

What is claimed is:

1. A compound of the formula

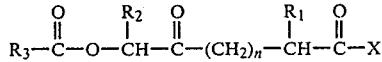

or a pharmaceutically acceptable salt thereof wherein:

X is

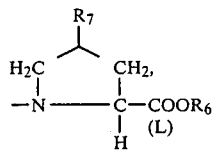

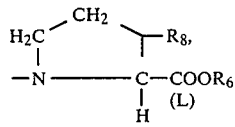

-continued

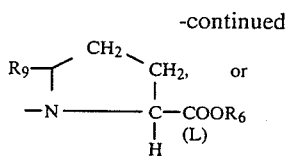

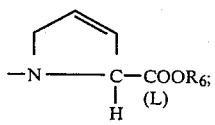

n is one or two;
R₁ is hydrogen, lower alkyl, halo substituted lower alkyl,

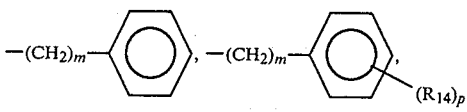

or —(CH₂)_m-cycloalkyl;
R₂ is lower alkyl,

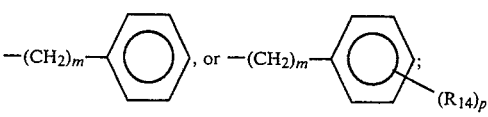

R₃ is lower alkyl,

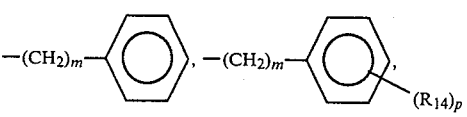

halo substituted lower alkyl, or —(CH₂)_m-cycloalkyl;
R₇ is hydrogen, lower alkyl, halogen, keto, hydroxy,

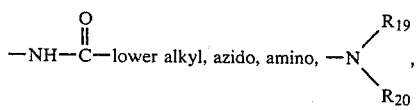

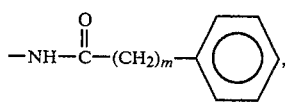

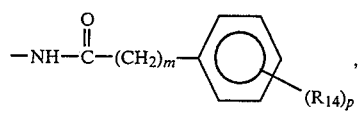

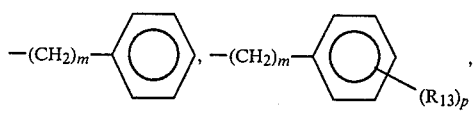

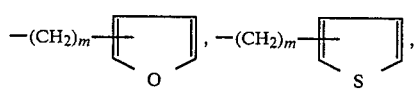

-continued

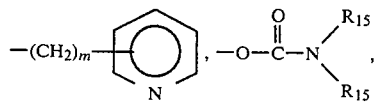

a 1- or 2-naphthyl of the formula

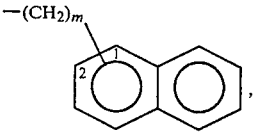

a substituted 1- or 2-naphthyl of the formula

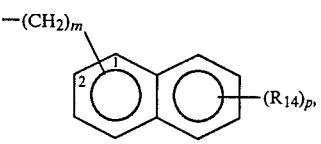

—(CH₂)_m—cycloalkyl, —O—lower alkyl,

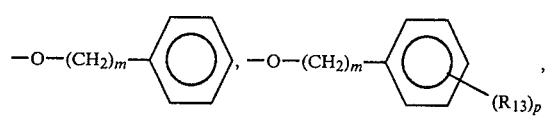

a 1- or 2-naphthyloxy of the formula

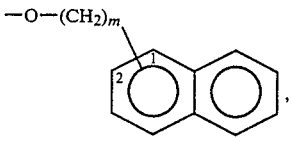

a substituted 1- or 2-naphthyloxy of the formula

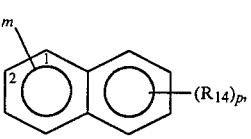

—S—lower alkyl, 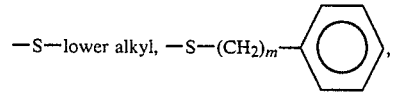

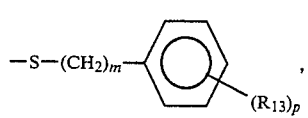

a 1- or 2-naphthylthio of the formula

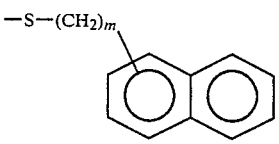

or a 1- or 2-substituted naphthylthio of the formula

-continued

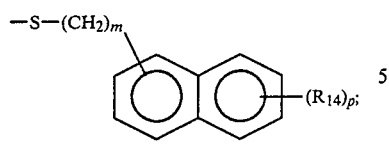

$R_8$ is keto, halogen,

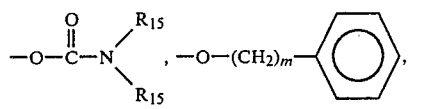

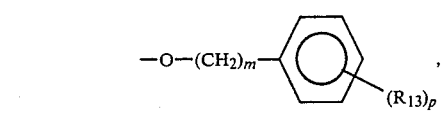

—O—lower alkyl, a 1- or 2-naphthyloxy of the formula

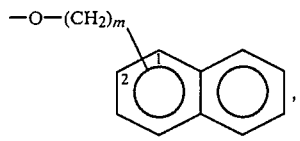

a substituted 1- or 2-naphthyloxy of the formula

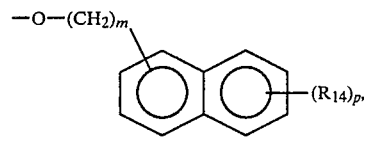

—S—lower alkyl, 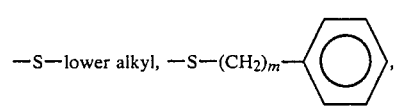

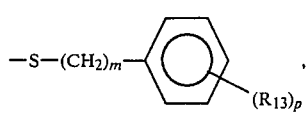

a 1- or 2-naphthylthio of the formula

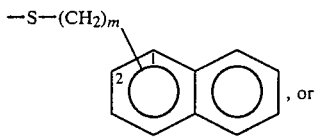

or a substituted 1- or 2- naphthylthio of the formula

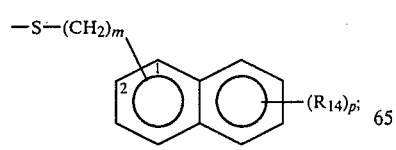

$R_9$ is keto,

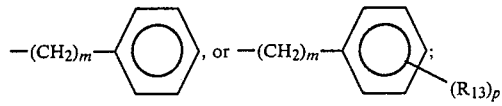

$R_{13}$ is lower alkyl or 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}$ is lower alkyl of 1 to 4 carbons, lower alkoxy of 1 to 4 carbons, lower alkylthio of 1 to 4 carbons, chloro, bromo fluoro, trifluoromethyl or hydroxy;

m is zero, one, two, three, or four;

p is one, two or three provided that p is more than one only if $R_{13}$ or $R_{14}$ is methyl, methoxy, chloro, or fluoro;

$R_6$ is hydrogen, lower alkyl, benzyl, benzhydryl, or

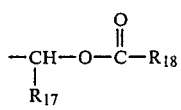

wherein $R_{17}$ is hydrogen, lower alkyl, cycloalkyl or phenyl, and $R_{18}$ is hydrogen, lower alkyl, lower alkoxy, phenyl, or $R_{17}$ and $R_{18}$ taken together are —(CH$_2$)$_2$—, —(CH$_2$)$_3$—, —CH=CH—, or

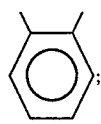

$R_{15}$ is hydrogen or lower alkyl of 1 to 4 carbons;
$R_{19}$ is lower alkyl, benzyl, or phenethyl; and
$R_{20}$ is hydrogen, lower alkyl, benzyl, or phenethyl.

2. A compound of claim 1 wherein:

$R_6$ is hydrogen, straight or branched chain lower alkyl of 1 to 4 carbons, or

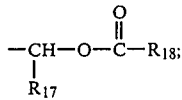

$R_7$ is hydrogen, hydroxy, straight or branched chain lower alkyl of 1 to 4 carbons, cyclohexyl, amino, —O-lower alkyl wherein lower alkyl is straight or branched chain of 1 to 4 carbons,

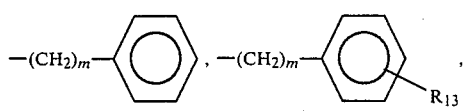

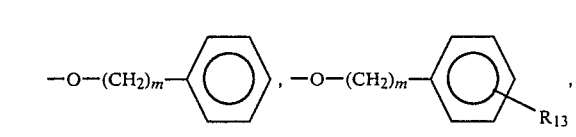

1-naphthyloxy, 2-naphthyloxy, —S-lower alkyl wherein lower alkyl is straight or branched chain of 1 to 4 carbons,

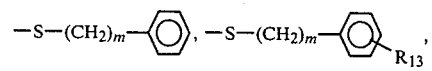

1-naphthylthio, or 2-naphthylthio;
R$_8$ is —O-lower alkyl wherein lower alkyl is straight or branched chain of 1 to 4 carbons, —S-lower alkyl wherein lower alkyl is straight ot branched chain of 1 to 4 carbons,

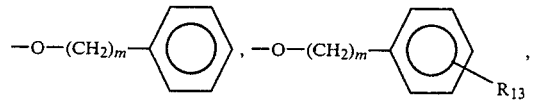

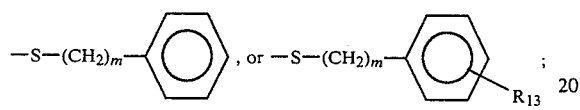

R$_9$ is phenyl, 2-hydroxyphenyl, or 4-hydroxyphenyl;
m is zero, one or two; R$_{13}$ is methyl, methoxy, methylthio, chloro, bromo, fluoro, or hydroxy;
R$_{17}$ is hydrogen, straight or branched chain lower alkyl of 1 to 4 carbons, or cyclohexyl; and
R$_{18}$ is straight or branched chain lower alkyl of 1 to 4 carbons or phenyl;
or an alkali metal salt thereof.

3. A compound of claim 2 wherein:
R$_2$ is

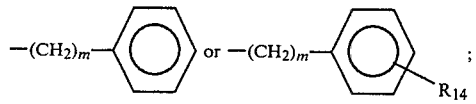

R$_3$ is

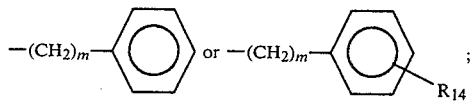

n is one;
R$_1$ is hydrogen, straight or branched chain lower alkyl of 1 to 4 carbons, CF$_3$,

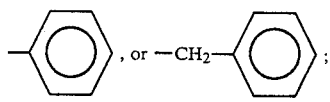

m is zero, one, or two; and
R$_{14}$ is methyl, methoxy, methylthio, chloro, bromo, fluoro, or hydroxy.

4. Compound of claim 3 wherein:
X is

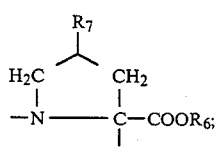

R$_7$ is hydrogen, cyclohexyl, lower alkoxy of 1 to 4 carbons,

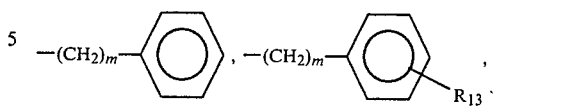

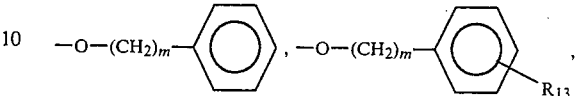

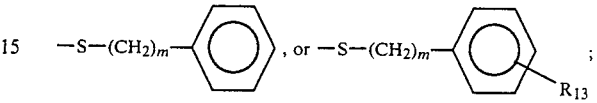

m is zero, one or two;
R$_{13}$ is methyl, methoxy, methylthio, chloro, bromo, fluoro, or hydroxy; and
R$_6$ is hydrogen, —C$_2$H$_5$,

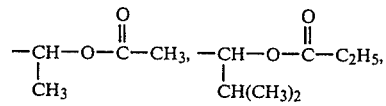

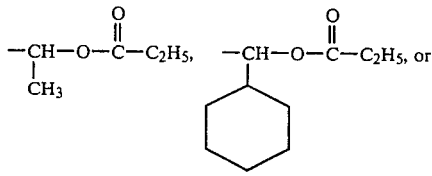

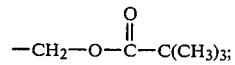

or an alkali metal salt thereof.

5. A compound of claim 4 wherein
R$_1$ is hydrogen or methyl;
R$_2$ is

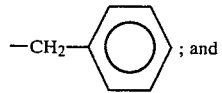; and

R$_3$ is

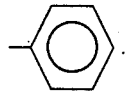

6. A compound of claim 5 wherein X is

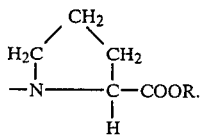

7. A compound of claim 6 wherein R$_1$ is hydrogen.
8. The compound of claim 7, 1-[(5S)-5-(benzoyloxy)-1,4-dioxo-6-phenylhexyl]-L-proline.
9. A compound of claim 6 wherein R$_1$ is methyl.
10. The compound of claim 9, 1-[(5S,2R)-5-(benzoyloxy)-2-methyl-1,4-dioxo-6-phenylhexyl]-L-proline.

* * * * *